United States Patent
Dillinger et al.

[11] Patent Number: 5,830,140
[45] Date of Patent: Nov. 3, 1998

[54] APPARATUS AND METHOD FOR REGISTERING SUBSTANCE-SPECIFIC AND ORGANISM-SPECIFIC ENERGETIC INFORMATION

[75] Inventors: Klaus Dillinger, St. Pölten; Christian Steiner, Viktring, both of Austria

[73] Assignee: Quintsysteme Fur Holopathische Medizin Ges.m.b.H., Polten, Austria

[21] Appl. No.: 561,666

[22] Filed: Nov. 22, 1995

[30] Foreign Application Priority Data

Nov. 23, 1994 [AT] Austria ................................ 446/94

[51] Int. Cl.⁶ .................................................. A61B 5/00
[52] U.S. Cl. ............................. 600/407; 600/409; 600/9; 607/50
[58] Field of Search ................. 128/653.1, 898, 128/735, 736, 907; 600/9, 11, 13, 14, 407, 409, 548, 549; 606/189; 607/50, 66, 115

[56] References Cited

U.S. PATENT DOCUMENTS

| | | |
|---|---|---|
| 5,092,835 | 3/1992 | Schurig et al. . |
| 5,144,554 | 9/1992 | Zhang et al. . |
| 5,162,037 | 11/1992 | Whitson-Fischman . |
| 5,192,263 | 3/1993 | Kraus . |
| 5,261,422 | 11/1993 | Kelly . |
| 5,458,142 | 10/1995 | Farmer et al. . |
| 5,481,196 | 1/1996 | Nosov . |
| 5,507,791 | 4/1996 | Sit'ko . |
| 5,526,811 | 6/1996 | Lypchuk . |
| 5,529,569 | 6/1996 | Woo . |
| 5,562,597 | 10/1996 | Van Dick . |
| 5,590,650 | 1/1997 | Genova . |
| 5,603,915 | 2/1997 | Nelson et al. . |

FOREIGN PATENT DOCUMENTS

| | | |
|---|---|---|
| 000 050 U1 | 10/1992 | Austria . |
| 9110 450 A1 | 7/1991 | WIPO . |
| WO 91/10450 | 7/1991 | WIPO . |
| 9202 201 A1 | 2/1992 | WIPO . |

OTHER PUBLICATIONS

EP 0 714 027 A3 European Search Report.
SU 894 373 Avenesov et al. 14 Feb. 1979.

*Primary Examiner*—Marvin M. Lateef
*Assistant Examiner*—Shawna J. Shaw
*Attorney, Agent, or Firm*—Herbert Dubno

[57] ABSTRACT

Substance-specific and body-specific information in the form of electromagnetic noise is stored after separation with bandpass filters so that individual noise spectra segments can reflect the different planes of the body system and stored information of this type can be combined with a carrier and used for therapy or used directly to activate an alcohol/water mixture and produce a homeopathic medicament.

22 Claims, 3 Drawing Sheets

APPARATUS AND METHOD FOR REGISTERING SUBSTANCE-SPECIFIC AND ORGANISM-SPECIFIC ENERGETIC INFORMATION

FIELD OF THE INVENTION

Our present invention relates to an apparatus and method of recording, registering or plotting of substance-specific and organism-specific (body-specific) energetic information in the form of electromagnetic spectra. The invention also relates to an apparatus or device and to a process for reproducing substance-specific and body-specific energetic information in the form of electromagnetic spectra, especially an apparatus and method for producing therapeutic radiation and an apparatus and method for producing activated or energetic medicaments.

BACKGROUND OF THE INVENTION

At room temperature every chemical substance will emit electromagnetic noise which contains information characteristic of the respective substance. On this principle are based holistic therapeutic processes which utilize substance-specific ultrafine oscillation information. Holistic therapies of this type include homeopathy in which the substance information is considered to apply by exchange in the potentiation of water clusters. Homeopathic remedies which are activated by the substance information, however, have been found to be extremely sensitive with respect to storage and the influence of electrical or magnetic fields in the region of the storage location. Such fields can disturb information contained in the homeopathic remedy and reduce or destroy the homeopathic effect.

The bioresonance effect is also based upon the principle of ultrafine oscillation information and is used, by transformation of the substance oscillations, for testing and elimination of allergies. The bioresonance field encompasses diagnostically and therapeutically the organ plane of the body system, the connective tissue plane and the autonomic or vegetative plane. Not affected by the bioresonance of the body system are the following planes:

The plane of voluntary muscle control (cerebellum, Sulcus Rolandi) with body feeling and movement centers and the superordinate cordical centers for translation of intentions. This plane is also associated with the drives (which can correspond to primitive intentions).

The plane of the sensory organs (eyes, ears, taste . . . plus their operating centers in the brain (visual cortex, aural cortex, etc.), but including all centers which serve for indirect sensory input and process them for life experience.

The plane of abstract thought that functions independently from body excitation or sensory excitation and reflects the higher functions of the ego. The corresponding brain centers according to Seitelberger and Eccles are probably distributed hologrammatically over the entire cerebrum.

In the practice of holistic medicine, the incorporation of these three planes is of considerable significance for diagnosis and therapy.

OBJECTS OF THE INVENTION

It is the principal object of the present invention to provide an apparatus and process which enables the registration and reproduction of substance-specific and body-specific energetic information in the form of electromagnetic spectra without the above-mentioned disadvantages.

It is also an object of the invention to provide an apparatus and process which can make available continuously, qualitatively high value homeopathic medicaments of optional composition or therapeutic application.

Still another object of the invention is to provide a device for therapy and diagnosis which can cover each of the six basic planes or regions, organs/connective tissue, support and mobility apparatus/vegetative or autonomic/voluntary musculature and drive including self-fulfillment/sensory organs and evaluation including practical experience/abstract thought (=ego), separately or collectively.

A further object of the invention is to provide a method of and an apparatus for therapeutic treatment or medicament preparation which will avoid drawbacks of earlier systems and which, especially in the field of homeopathy, will facilitate treatment of patients.

SUMMARY OF THE INVENTION

These objects and others which will become apparent hereinafter are attained, in accordance with the invention, in a device or apparatus for the plotting or registering of a spectrum which is body-specific or substance-specific and which comprises a contact element or pickup connected with an amplifier and in contact with the substance or body emitting the spectrum. Connected to the amplifier is an analog/digital converter which digitalizes the amplified signal. A data processing unit provided with an electronic storage medium is connected to the analog/digital converter and enables storage of the digitalized signal on the electronic storage medium. The apparatus, therefore, can comprise:

- a contact element juxtaposed with a substance emitting an electromagnetic spectrum corresponding to energy characteristics of the substance for collecting and transducing the electromagnetic spectrum into an electrical signal corresponding to the electromagnetic spectrum;
- an amplifier connected to the contact element for amplifying the electrical signal corresponding to the electromagnetic spectrum to produce an amplified electrical signal;
- an analog/digital converter connected to the amplifier for digitalizing the amplified electrical signal to produce a digitalized signal; and
- a data processor connected to the analog/digital converter and provided with an electronic storage medium for storage of the digitalized signal.

Preferably the apparatus has individually controllable bandpass filters whose frequency regions (pass bands) correspond to homeopathic powers or to the following basic regions: organs; connective tissue, support apparatus and movement apparatus; autonomous or vegetative system, voluntary muscle control and drives (i.e. self-fulfillment); sensory organs and evaluation (i.e. life experience or practical experience); abstract thought (i.e. ego).

Advantageously, the bandpass filters can correspond to the six frequency regions of the homeopathic powers D3, D4, D12, D21, D30 and D200.

As far as a process for registering the substance-specific and energetic information in the form of electromagnetic spectra is concerned, it may comprise the steps of:

- a) juxtaposing a contact element with a substance emitting an electromagnetic spectrum corresponding to energy characteristics of the substance and transducing the electromagnetic spectrum emitted by the substance into an electrical signal corresponding to the electromagnetic spectrum;
- b) amplifying the electrical signal corresponding to the electromagnetic spectrum to produce an amplified electrical signal;

c) digitalizing the amplified electrical signal in an analog/digital converter to produce a digitalized signal; and d) storing at least a portion of the digitalized signal in an electronic storage medium of a data processor.

The digitalized signal, according to the invention, prior to storage in the data processor can be subjected to an error compensation to correct for signal falsification by intrinsic oscillation of the data processor.

The apparatus and method of the invention for registering substance-specific energetic information can be used for practically unlimited preservation of the energetic information and for any purpose that such information may serve, e.g. for reproduction to generate medicaments as will be described hereinafter or even for therapeutic purposes and direct treatment of the human organism or patient.

The apparatus according to the invention for reproduction of substance-specific energetic information in the form of electromagnetic spectra utilizing an electronic storage can comprise electronic storage having the spectra stored therein and, in accordance with this invention, a data processor connected to the storage for selectively outputting substance-specific spectra from the storage in the form of digital signals;

a digital/analog converter connected to the data processor for converting the digital signals to analog signals; and an outputting element connected to the digital/analog converter for outputting analog signals.

The process or method of reproducing the substance-specific energetic information can comprise:

a) storing at least one substance-specific spectrum selectively in a storage medium of a data processor in digital form;

b) outputting a digital signal representing the stored spectrum;

c) converting the digital signal into an analog in a digital/analog converter;

d) amplifying the analog signal; and e) outputting an amplified analog signal with at least one electrode.

The apparatus and method of reproduction can be used to generate therapeutic radiation or for the production of energetic medicaments as noted. The data processor enables optional processing of the digitalized spectrum, for example, an inversion thereof, a summing of several spectra or the weighting of the individual spectra before summation, thereby enabling control of the results of the therapy and production of the medicaments.

The apparatus and method thus result in a kind of "digital homeopathy" in which, for example, the lower frequency components of the oscillation spectra are digitalized, stored in a data processor, modified and transformed into analog signals for use in therapy or the preparation of medicaments.

The reproduced substance oscillations can be used for all disciplines of energetic medicine for diagnosis and therapy. By corresponding measurements on patients (e.g. by means of electro-acupuncture according to Voll), energetic effects of digital sampled substance oscillations on the human body fully equivalent to those of pure substance probes or pure homeopathic medicaments can be obtained and thus a higher quality of treatment than that which can correspond to analog mimicking of the pure substance probes. The substance probes themselves are susceptible to electrical and magnetic fields and thus cannot be effectively stored for prolonged periods. Naturally the digital "substance probes" in accordance with the invention do not undergo any change with aging and remain effective in the original "quantity" and "purity."

In digital form the substance oscillations can be processed optionally by computer programs and thus can be utilized for diagnostic and therapeutic purposes with a high level of effectiveness, convenience and comfort than earlier homeopathic remedies.

The digitalized form of the substance oscillations of the invention has numerous advantages including:

a) several thousand digitalized substance probes can be stored on a single CD-ROM, b) the homeopathic potentiation of substances can be software controlled, c) the software-controlled mixture of optionally selected digitalized substance probes for different homeopathic powers is possible in optional mixing preparations to yield a virtual homeopathic complex, d) the software-controlled inversion of digitalized substance probes is possible (corresponding to inversion of the substance oscillations, e.g. for allergy cures), e) computer-supported automated allergy reactions can be carried out, f) computer-supported therapy upon transformation of substance oscillations upon patients, e.g. allergy cures by bioresonance, can be practiced, and g) the formation of energetic medicaments and the evaluation of them by computer supported research and the introduction of substance information from stored or synthesized substance information to alcohol-water mixtures is possible, e.g. with the formation of allergy drops or the like.

The apparatus according to the invention for reproducing body-specific energetic information in the form of electromagnetic oscillations can comprise an analog storage in which body-specific spectra have been previously stored and an amplifier following which individually-controllable bandpass filters are provided. The output signals from these bandpass filters can be combined in an optional manner by a logic unit and, preferably, the frequency ranges of the bandpass filters correspond to the homeopathic powers previously described or the following specific regions of the organism: organs; connective tissue, support apparatus and movement apparatus; autonomous or vegetative system, voluntary muscle control and drives (i.e. self-fulfillment); sensory organs and evaluation (i.e. life experience or practical experience); abstract thought (i.e. ego).

The apparatus can further include a generator for producing a carrier wave. With the apparatus of the invention serving as a therapeutic apparatus, the output element or elements can include two magnetic heads, and, if desired, an excitation current manual electrode from which feedback oscillation from the patient is applied to the circuit.

According to a feature of the invention, the body-specific spectra can be stored in the crystal lattice of a solid. The body-specific spectra can be spectra derived from healthy individuals.

In the apparatus aspect, the reproduction of body-specific energetic information can store the electromagnetic oscillations in the analog storage medium and can read out stored body-specific spectra from the latter, analyze the read-out spectra via an amplifier and apply the amplified signal to one or more bandpass filters. As noted, the output signals of the bandpass filters are optionally combined in the logic and the combined signal is fed to one or more electrodes. The amplified output signal of the logic can be superimposed on a carrier wave similar to a Schuhmann wave to produce the therapeutically-effective oscillations. The carrier wave can be a combination of a 10 Hz magnetic field with 1 MHz pulses. Preferably feedback of oscillations intrinsic to the patient can be superimposed on the body-specific spectrum to generate a resonance state.

Here again the apparatus and method enable diagnostic and therapeutic action on all body systems including each of the six basic regions: organs; connective tissue, support apparatus and movement apparatus; autonomous or vegetative system, voluntary muscle control and drives (i.e. self-fulfillment); sensory organs and evaluation (i.e. life experience or practical experience); abstract thought (i.e. ego), each with a predetermined frequency band constituting the homeopathic signals for each of these planes.

Conversely, from the quasiunlimited frequency spectrum of the body, by the application of filters corresponding to the aforementioned frequency bands, specific information for the individual planes can be obtained which can be therapeutically utilized in the same manner as with earlier bioresonance therapy. In the system of the invention, classical acupuncture meridians can be activated with electronically altered, e.g. inverted, potential oscillations or other points can be activated or activation can be effected by the hand or foot of the patient.

The points can be manually selected or preprogrammed, for example, the infrared oscillations of substances, for instance body secretions, can be electronically detected and within certain frequency ranges or in inverted form transmitted to the patient to achieve homeopathic effects, for example, the quenching of allergic conditions.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
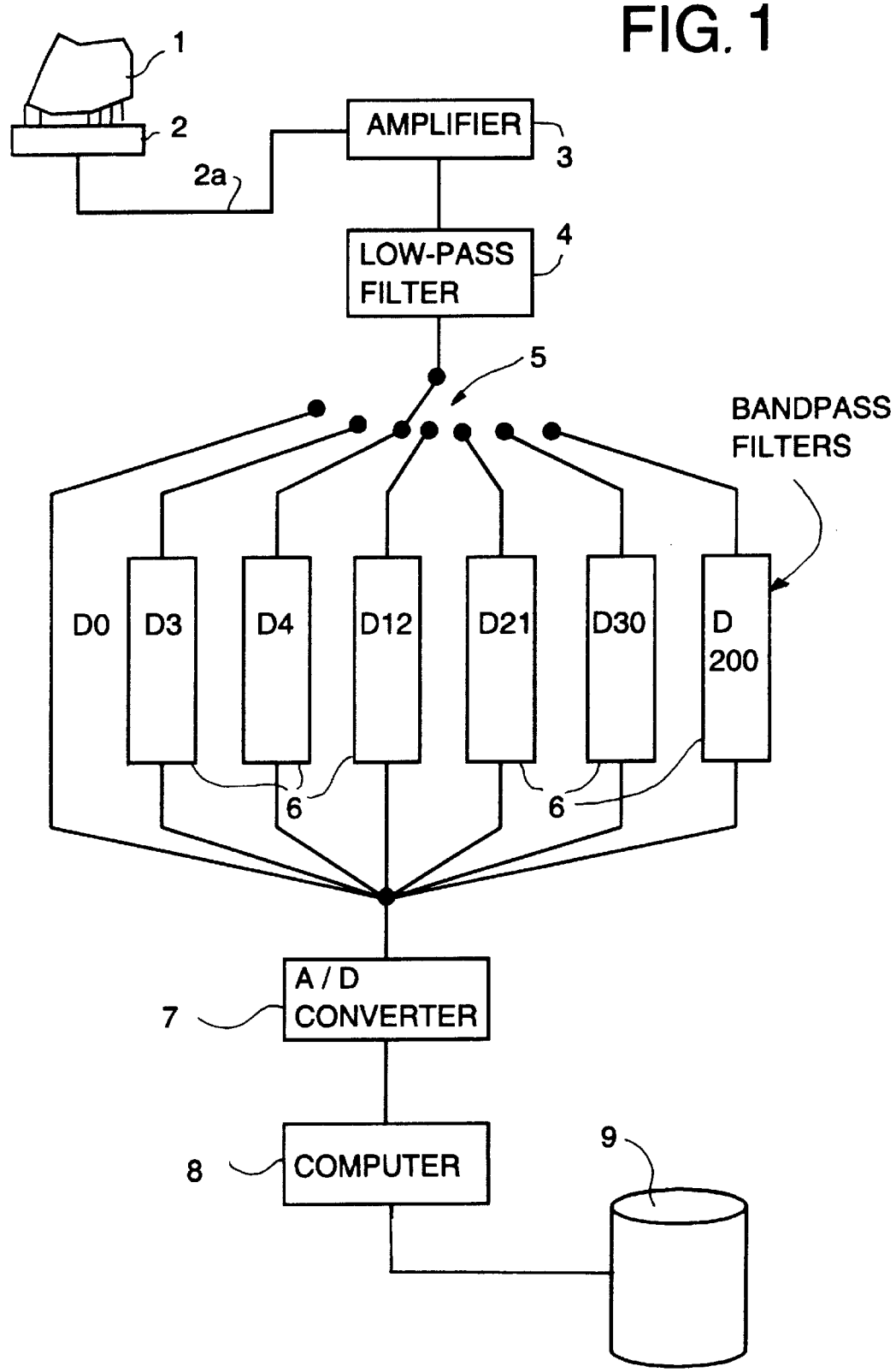
FIG. 1 is a block diagram of an apparatus for the pick-up of substance-specific information according to the invention.

The apparatus shown in FIG. 1 for detecting substance-specific electromagnetic spectra from a sample 1 of a substance comprises a brass plate 2 which serves as a contact medium for the substance-specific long-wave electro-magnetic noise and effectively constitutes a transducer, supply an electrical signal on the line 2a representing the electro-magnetic noise spectrum.

Connected to the contact element or sensor 2 is an amplifier 3 which amplifies the noise spectrum from the brass plate. The amplified noise spectrum is supplied through a low-pass filter 4 and a manual switch 5 selectively to one of six bandpass filters 6. The switch is operated by the practitioner to select the desired homeopathic potential. The pass bands of the filters, i.e. the filter frequencies and the homeopathic potentials are related as shown in the following table:

| POWER | FILTER FREQUENCIES |
| --- | --- |
| D0 (Original substance) | 0–22 Khz |
| D3 | 0–3.5 Khz |
| D4 | 3.5–7 Khz |
| D12 | 7–10.5 Khz |
| D21 | 10.5–14 Khz |
| D30 | 14–18 Khz |
| D200 | 18–22 Khz |

The selected pass band is then fed to an analog/digital converter 7 with a sampling rate of 44.1 Khz with a resolution of 16 bits per second for digital sampling.

The digitalized signal is applied to a computer 8 whose software can allow error compensation through an appropriate algorithm. The error compensation is required to extract from the picked-up and reproduced electro-magnetic signals, the electro-magnetic intrinsic oscillation of the computer system.

The oscillation data, freed from superimposed intrinsic signals characteristic of the computer system, are registered in a data bank or memory 9 which can be an optical storage medium such as a CD-ROM.

In practice, therefore, the substance to be analyzed is placed upon the contact element and in the storage or memory, the portion of the noise spectrum corresponding to the pass band for each of the selected powers D0, D3, D4, D12, D21, D30 and D200 is separately stored.

Figure 2:
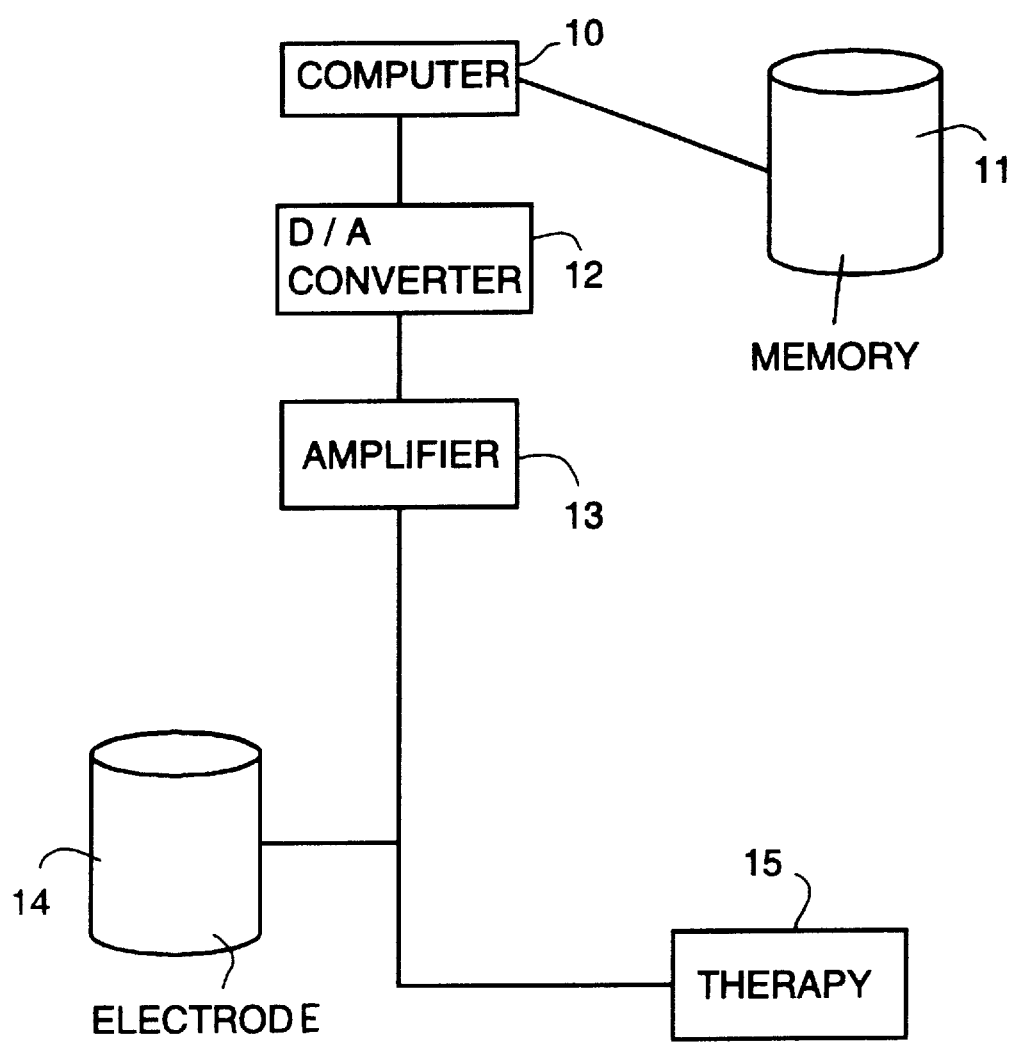
FIG. 2 is a block diagram of an apparatus for reproducing substance-specific information.

An apparatus for reproducing the electro-magnetic spectrum and thus, homeopathically, the substance sample, has been shown in FIG. 2.

The computer 10 can read the particular electronic spectrum, depending upon the power desired, from the digital storage medium 11 which effectively is an electronic data bank storing the electronic substance samples. The computer is programmed to allow mixing of the electronic samples for any required homeopathic power. The electronic substance samples can be added, modified by, say the inversion for the treatment of allergies or added after such inversion.

The resulting data is fed to a digital/analog converter 12 and as an analog signal, is unloosely repeated via a feedback loop in accordance with the computer program so that the original digital signal, having a duration of only one second, can be repetitively reproduced as the analog signal for activation of a solution to form a medicament or for therapeutic purposes.

The analog signal, amplified at 13 can be fed to a therapy device 15 which represents application of the signal to a patient or to a container electrode 14 representing activation of a substance, e.g. an alcohol/water mixture to create a homeopathic medicament with the stored substance information.

Figure 3:
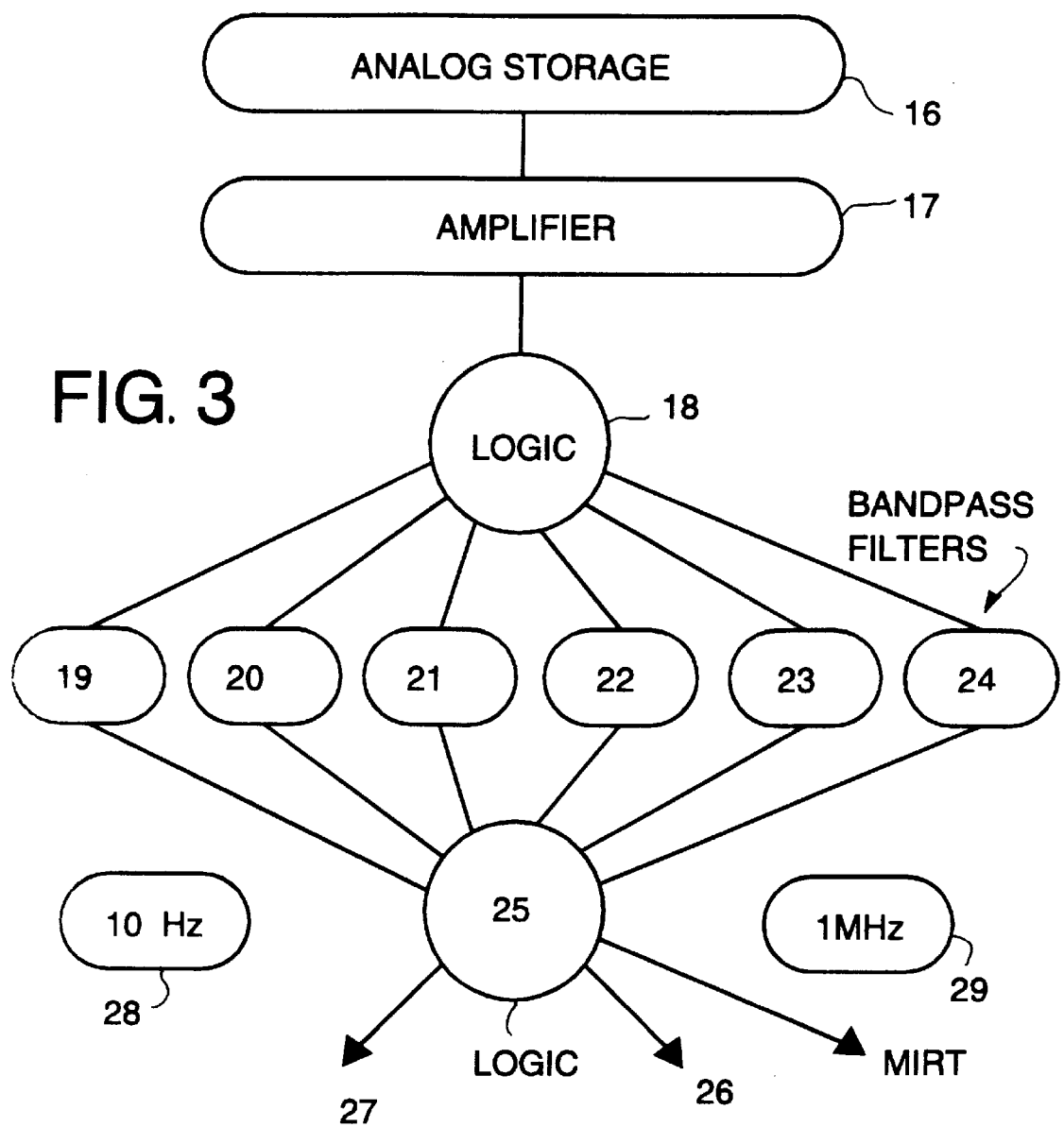
FIG. 3 is a diagram of an apparatus for use in therapy.

The apparatus of FIG. 3 contains an analog storage 16 in which the potential oscillations of significant acupuncture points of a normal reference individual can be stored and from which the potential oscillations of these acupuncture points can be read. The respective spectrum is amplified at 17 and then fed to a logic 18. The bandpass filters 19–24 can be individually controlled and rendered effective individually or in any combination or with appropriate inversion. The output signals of the bandpass filter thus can be combined in a further logic 25 to generate a therapeutic magnetic field which can be applied by magnetic heads 26, 27 to the patient or used in minimal activation current therapy (MIRT).

Figure 4:
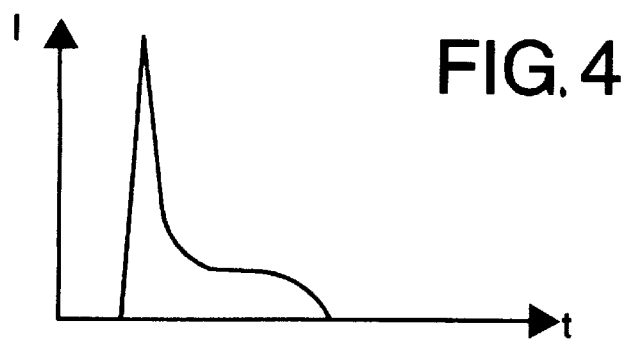
FIG. 4 is a graph of the waveform of a carrier electromagnetic field.

Characteristic oscillation information after processing through the bandpass filters can be superimposed on an oscillating 10 Hz magnetic field from the generator 28 and a 1 MHz pulse from the generator 29. The resulting carrier wave has been represented in FIG. 4 in which the current wave form is plotted as a function of time. The resulting carrier has an oscillation information superimposed thereon and has been found to penetrate deeply into tissue and produce resonance phenomena. The effect is amplified by the minimal energization current therapy in which the applied weak current, say three volts, is pulsed simultaneously like the magnetic field and forms a carrier for the oscillation information although on a galvanic basis.

The magnetic field serving as a carrier largely corresponds to the Schuhmann wave which has a characteristic of a standing wave between the surface of the earth and the magnetosphere. This wave form has been found to be optimum as a carrier for biological relevant information since mankind has adapted to it over time and is maximally in resonance therewith.

Both in diagnosis (in accordance with the patterns of electro-acupuncture) and in therapy (magnetic field therapy combined with a minimum activation current therapy) the stored signals can be superimposed on magnetic fields or activation currents to activate the respective planes determined by the bandpass filters which were selected. With fine control of the apparatus of the invention, for example, phase shifting of the 10 Hz signals at the magnetic heads, different mixtures of high frequency signals can be produced which can allow within the first plane, for example, individual organs to be targeted or the poor functioning of the connective tissue, supporting apparatus and movement apparatus (second plane) or the detailed functioning of the central nervous system (planes 4–6) to be enhanced.

During the therapy, the patient's own intrinsic oscillations, detected by hand or from selected acupuncture points, can be processed through the same computer control and fed back as part of the therapeutic signal to create a therapeutic resonance. The stored reference oscillations as well as the processed patient oscillations can be targeted at the six hierarchal main systems and their subsystems to maximize diagnostic and therapeutic treatment.

We claim:

1. An apparatus for registering substance-specific energetic information in a form of electromagnetic spectra, comprising:

a contact element juxtaposed with a substance which has homeopathic-treatment capability and emitting an electromagnetic spectrum corresponding to energy characteristics of said substance having homeopathic-treatment capability and for collecting and transducing said electromagnetic spectrum into an electrical signal corresponding to said electromagnetic spectrum;

an amplifier connected to said contact element for amplifying said electrical signal corresponding to said electromagnetic spectrum to produce an amplified electrical signal;

an analog/digital converter connected to said amplifier for digitalizing said amplified electrical signal to produce a digitalized signal; and a data processor connected to said analog/digital converter and provided with an electronic storage medium for storage of said digitalized signal.

2. The apparatus defined in claim 1, further comprising respective bandpass filters connected between said contact element and said data processor for discriminating between frequency ranges of different homeopathic powers.

3. An apparatus for registering substance-specific energetic information in a form of electromagnetic spectra, comprising:

a contact element juxtaposed with a substance which has homeopathic-treatment capability emitting an electromagnetic spectrum corresponding to energy characteristics of said substance for collecting and transducing said electromagnetic spectrum into an electrical signal corresponding to said electro-magnetic spectrum;

an amplifier connected to said contact element for amplifying said electrical signal corresponding to said electromagnetic spectrum to produce an amplified electrical signal;

an analog/digital converter connected to said amplifier for digitizing said amplified electrical signal to produce a digitized signal;

a data processor connected to said analog/digital converter and provided with an electronic storage medium for storage of said digitized signal; and bandpass filters connected between said contact element and said data processor for discriminating between frequency ranges of different homeopathic powers, six of said bandpass filters being provided with respective pass bands for homeopathic powers D3, D4, D12, D21, D30 and D200.

4. An apparatus for registering substance-specific energetic information in a form of electromagnetic spectra, comprising:

a contact element juxtaposed with a substance which has homeopathic-treatment capability and emitting an electromagnetic spectrum corresponding to energy characteristics of said substance having homeopathic-treatment capability and for collecting and transducing said electromagnetic spectrum into an electrical signal corresponding to said electromagnetic spectrum;

an amplifier connected to said contact element for amplifying said electrical signal corresponding to said electromagnetic spectrum to produce an amplified electrical signal;

an analog/digital converter connected to said amplifier for digitalizing said amplified electrical signal to produce a digitalized signal; and a data processor connected to said analog/digital converter and provided with an electronic storage medium for storage of said digitalized signal;

respective bandpass filters connected between said contact element and said data processor for discriminating between frequency ranges of the following basic regions of a human organism: body organs; connective tissue, supporting apparatus and movement apparatus; autonomic system; voluntary muscular control system and drives, self-fulfillment; sensory organ and evaluation, and practical experience system; and abstract thought and ego.

5. A process for registering substance-specific energetic information in a form of electromagnetic spectra, comprising the steps of:

a) juxtaposing a contact element with a substance having homeopathic-treatment capability and emitting an electromagnetic spectrum corresponding to energy characteristics of said substance having homeopathic-treatment capability and transducing the electromagnetic spectrum emitted by said substance into an electrical signal corresponding to said electromagnetic spectrum;

b) amplifying the electrical signal corresponding to said electromagnetic spectrum to produce an amplified electrical signal;

c) digitalizing said amplified electrical signal in an analog/digital converter to produce a digitalized signal;

d) storing at least a portion of the digitalized signal in an electronic storage medium of a data processor; and separating said amplified electrical signal prior to the digitizing thereof into respective frequency bands by respective bandpass filters corresponding to different homeopathic powers, characteristic signals for each of the homeopathic powers being stored separately, said amplified electrical signal being divided selectively by six bandpass filters into pass bands corresponding to respective frequency ranges for homeopathic powers D3, D4, D12, D21, D30 and D200.

6. A process for registering substance-specific energetic information in a form of electromagnetic spectra, comprising the steps of:

a) juxtaposing a contact element with a substance having homeopathic-treatment capability and emitting an electromagnetic spectrum corresponding to energy characteristics of said substance having homeopathic-treatment capability and transducing the electromagnetic spectrum emitted by said substance into an electrical signal corresponding to said electromagnetic spectrum;

b) amplifying the electrical signal corresponding to said electromagnetic spectrum to produce an amplified electrical signal;

c) digitalizing said amplified electrical signal in an analog/digital converter to produce a digitalized signal;

d) storing at least a portion of the digitalized signal in an electronic storage medium of a data processor; and, e) subjecting the digitalized signal prior to storage to an error compensation to correct for signal falsification by an intrinsic oscillation superimposed thereon by the data processor.

7. A method of reproducing substance-specific energetic information in a form of electromagnetic oscillations, comprising the steps of:

a) storing at least one substance-specific spectrum selectively in a storage medium of a data processor in digital form;

b) outputting a digital signal representing the stored spectrum;

c) converting the digital signal into an analog in a digital/analog converter;

d) amplifying the analog signal; and e) outputting an amplified analog signal by electrically energizing an electrode therewith, stored spectra being read from storage prior to conversion into the analog signal, and signals representing the spectra read from storage being inverted, optionally weighted and summed, the summed signals being repetitively outputted over a predetermined time interval.

8. The method defined in claim 7 wherein said electrode is constructed and arranged for application to a patient for treating the patient with therapeutic electromagnetic oscillations corresponding to the stored spectrum.

9. The method defined in claim 7 wherein the stored spectrum is one of a multiplicity of stored spectra in respective frequency bands corresponding to respective homeopathic potentials with the frequency bands of the respective homeopathic potentials being separately stored and recovered from storage.

10. The method defined in claim 7 wherein said electrode outputs energetic information corresponding to at least one substance and is used to generate an energetic medicament.

11. An apparatus for reproducing organism-specific energetic information in a form of electromagnetic oscillations, comprising:

an analog storage with organism-specific spectra stored therein;

an amplifier connected to said storage for outputting amplified organism-specific spectral signals;

independently controllable bandpass filters connected to said amplifier for providing respective output frequency ranges corresponding to different homeopathic powers for affecting the following basic regions of a human organism: body organs; connective tissue, supporting apparatus and movement apparatus; autonomic system; voluntary muscular control system and drives, self-fulfillment; sensory organ and evaluation, and practical experience system; and abstract thought and ego;

a logic connected to said bandpass filters for optionally combining outputs thereof; and an output element connected to said logic for applying logically-combined signals from said bandpass filters to the body.

12. The apparatus defined in claim 11 wherein six bandpass filters are provided with bandpass frequency ranges corresponding respectively to homeopathic powers D3, D4, D12, D21, D30 and D200.

13. The apparatus defined in claim 11, further comprising a carrier wave generator connected to said logic.

14. The apparatus defined in claim 11 wherein said output element comprises two magnetic heads and optionally a stimulating current manual electrode.

15. The apparatus defined in claim 11, further comprising manual electrode for introducing oscillations characteristic of the patient to said amplifier.

16. The apparatus defined in claim 11 wherein the organism-specific spectra are stored in the crystal lattice of a solid body.

17. The apparatus defined in claim 14 wherein the organism-specific spectra are spectra of healthy individuals.

18. A method of reproducing organism-specific energetic information in a form of electromagnetic oscillations comprising the steps of:

a) storing organism-specific spectra in an analog storage;

b) selectively withdrawing analog spectra from said storage and amplifying same in at least one amplifier;

c) dividing an amplified signal from said amplifier into a plurality of frequency ranges through at least one band-pass filter connected to said amplifier to produce respective outputs corresponding to said frequency ranges;

d) logically and selectively combining said outputs; and e) generating at an output element an output signal from the logical combination of said outputs, said bandpass filter having outputs corresponding to respective homeopathic powers for corresponding to the following basic regions of a human apeutism: body organs; connective tissue, supporting apparatus and movement apparatus; autonomic system; voluntary muscular control system and drives, self-fulfillment; sensory organ and evaluation, and practical experience system; and abstract thought and ego.

19. The process defined in claim 18 wherein a plurality of bandpass filters are provided with respective pass bands in tfrequency ranges corresponding to the homeopathic powers D3, D4, D12, D21, D30 and D200.

20. The process defined in claim 18 wherein the amplified signal are superimposed upon a carrier wave of the Schuhmann type.

21. The process defined in claim 20 wherein the carrier wave is a 10 Hz magnetic field with 1 MHz pulses.

22. The process defined in claim 18, further comprising the step of superimposing on the signal applied by said element a patient's own oscillations to generate a resonance state.

* * * * *